(12) United States Patent
O'Neal et al.

(10) Patent No.: US 11,718,818 B2
(45) Date of Patent: Aug. 8, 2023

(54) BIOREACTOR WITH INTEGRATED FLUE GAS DISTRIBUTION

(71) Applicant: ExxonMobil Technology and Engineering Company, Annandale, NJ (US)

(72) Inventors: Everett J. O'Neal, Asbury, NJ (US); Patrick L. Hanks, Bridgewater, NJ (US); Kevin B. Daly, Jersey City, NJ (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 61 days.

(21) Appl. No.: 16/891,119

(22) Filed: Jun. 3, 2020

(65) Prior Publication Data

US 2021/0047596 A1 Feb. 18, 2021

Related U.S. Application Data

(60) Provisional application No. 62/887,704, filed on Aug. 16, 2019.

(51) Int. Cl.
| | | |
|---|---|---|
| *C12M 1/00* | (2006.01) | |
| *C12M 1/26* | (2006.01) | |
| *C12M 1/34* | (2006.01) | |
| *C12M 1/04* | (2006.01) | |
| *A01G 33/00* | (2006.01) | |

(52) U.S. Cl.
CPC ............ *C12M 21/02* (2013.01); *C12M 23/18* (2013.01); *C12M 27/04* (2013.01); *C12M 29/00* (2013.01); *C12M 33/04* (2013.01); *C12M 41/40* (2013.01); *C12M 41/44* (2013.01); *A01G 33/00* (2013.01)

(58) Field of Classification Search
CPC ...... C12M 21/02; C12M 23/18; C12M 27/04; C12M 29/00; C12M 33/04; C12M 41/40; C12M 41/44; A01G 33/00
See application file for complete search history.

(56) References Cited

U.S. PATENT DOCUMENTS

| | | | |
|---|---|---|---|
| 4,237,008 A * | 12/1980 | Ratigan .................. | C02F 1/686 210/205 |
| 8,110,395 B2 | 2/2012 | Lewnard et al. | |
| 2009/0068727 A1 * | 3/2009 | Karr ...................... | C12M 29/00 435/292.1 |
| 2009/0148927 A1 * | 6/2009 | Schroeder .............. | C12M 23/04 435/257.1 |
| 2009/0305389 A1 * | 12/2009 | Willson ................. | C12M 23/14 156/60 |
| 2010/0068801 A1 * | 3/2010 | Woods ................... | C12M 27/20 435/292.1 |
| 2011/0281340 A1 * | 11/2011 | Turner ................... | C12M 21/02 435/257.1 |

(Continued)

*Primary Examiner* — William H. Beisner
*Assistant Examiner* — Danielle B Henkel
(74) *Attorney, Agent, or Firm* — Shook, Hardy & Bacon L.L.P.

(57) ABSTRACT

A system includes a photobioreactor that provides a channel configured to contain an algae slurry, a duct positioned adjacent the channel and configured to convey a gas, and a barrier separating the duct from the channel and providing one or more apertures to allow a portion of the gas to be injected into the algae slurry from the duct.

20 Claims, 2 Drawing Sheets

(56) References Cited

U.S. PATENT DOCUMENTS

2011/0307976 A1    12/2011  Ploechinger
2012/0295337 A1*   11/2012  Navarro .................. C12M 29/06
                                                        435/257.1
2013/0109085 A1*    5/2013  Woods ................... C12M 23/26
                                                        435/292.1

* cited by examiner

US 11,718,818 B2

BIOREACTOR WITH INTEGRATED FLUE GAS DISTRIBUTION

CROSS-REFERENCE TO RELATED APPLICATIONS

This application claims the benefit of U.S. Provisional Application No. 62/887,704 filed Aug. 16, 2019, which is herein incorporated by reference in its entirety.

BACKGROUND OF THE INVENTION

The present disclosure is related to growing algae for biofuel production and, more particularly, to delivering flue gas or another gas for algae growth.

Concerns about climate change, carbon dioxide ($CO_2$) emissions, and depletion of subterranean oil and gas resources have led to widespread interest in the production of biofuels from algae and microalgae. As used herein, the term "biofuel" refers to any type of fuel produced from algae, and the term "algae" will include microalgae, unless explicitly distinguished.

As compared to some other plant-based biofuel feedstocks, algae have higher $CO_2$ fixation efficiencies and growth rates, and growing algae can efficiently utilize wastewater and industrial gases as nutrient sources. The biomass of algae stores increasing quantities of lipids as it grows. Methods for harvesting and utilizing algae involve extracting and converting their stored lipids and carbohydrates into renewable biofuels, such as diesel and jet fuel, or into other hydrocarbons, as examples.

Algae biomass is generally grown in a water slurry contained in a light-driven bioreactor or "photobioreactor" (PBR) using photosynthetic algae strains. Types of photobioreactors include open and closed ponds and closed or open reactor vessels, as examples. Various strains of algae are classified as photoautotrophic organisms, or organisms that can survive, grow and reproduce with energy derived entirely from the sun through the process of photosynthesis. Photosynthesis, aided by other cellular biochemical processes, is essentially a carbon recycling process through which inorganic $CO_2$ is absorbed and combined with solar energy, nutrients, and water to synthesize carbohydrates, lipids, and other compounds necessary to algae life. In addition to production of lipids and carbohydrates for biofuel production, the benefits of growing and harvesting algae includes utilization of $CO_2$ and production of oxygen.

The $CO_2$ used for algae growth may come from any suitable source, including atmospheric air, flue gas/exhaust streams from a combustion process, or a storage location including tanks or geological formations, as examples. Flue gases may also provide usable nitrogen for algae growth. Various methods for delivering flue gas and other sources of $CO_2$ to photobioreactors have been proposed with varying degrees of success and complication. Therefore, an algae growth system that provides improvements to the delivery of $CO_2$ or usable nitrogen for algae growth would be desirable.

SUMMARY

The present disclosure is related to growing algae for biofuel production and, more particularly, to delivering flue gas or another gas for algae growth, including the distribution of the gases within bioreactors.

In some embodiments, a system for growing algae, as disclosed herein, includes a photobioreactor that provides a channel configured to contain an algae slurry, a duct positioned adjacent the channel and configured to convey a gas, and a barrier separating the duct from the channel and providing one or more apertures to allow a portion of the gas to be injected into the algae slurry from the duct.

In some embodiments, a method, as disclosed herein, includes containing an algae slurry within a channel of a photobioreactor, conveying a gas within a duct positioned adjacent the channel, wherein the duct and the channel are separated by a barrier that provides one or more apertures, and injecting at least a portion of the gas into the algae slurry through the one or more apertures.

In some embodiments, a photobioreactor, as disclosed herein, includes a pond volume configured to contain an algae slurry, a duct positioned adjacent the pond volume and configured to convey a gas, and a barrier separating the duct from the pond volume and comprising a plurality of apertures through which the gas is injected into the algae slurry from the duct.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
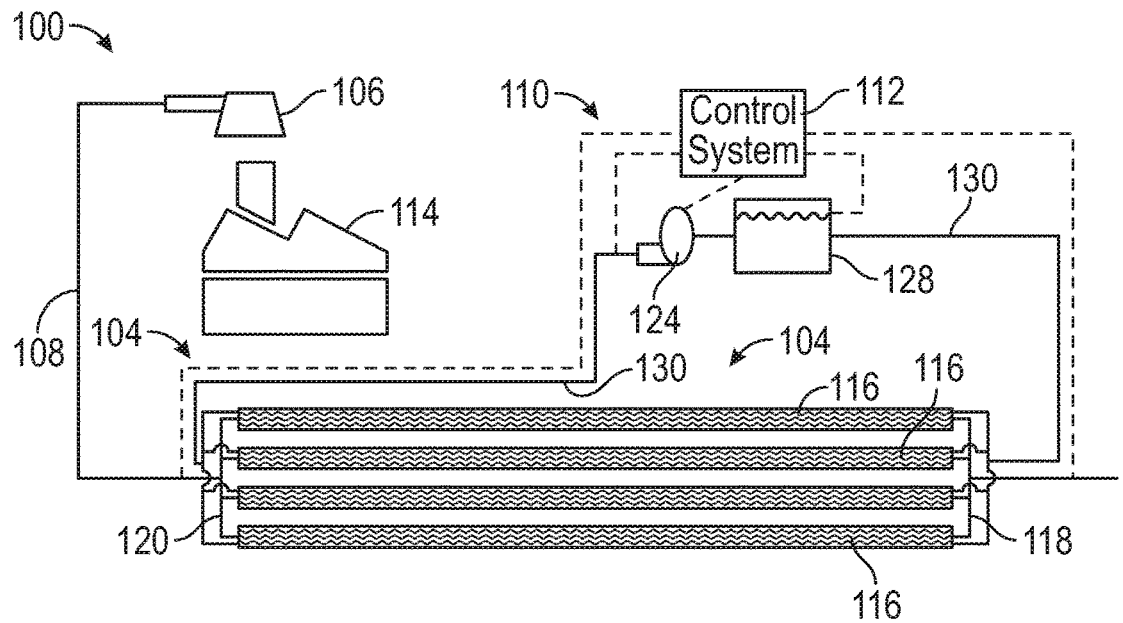
FIG. 1 is a schematic diagram of an example system for growing algae, according to various embodiments of the present disclosure.

The present disclosure is related to growing algae for biofuel production and, more particularly, to delivering flue gases or another gas for algae growth, including the distribution of the gases within bioreactors.

This disclosure combines unique gas ducts and algae photobioreactor ponds for biofuels synthesis. The disclosed apparatus or systems include a gas duct extending beneath or alongside an algae photobioreactor pond and separated by a barrier. The barrier may provide or define selectively located apertures to serve as pathways for gases from the duct to bubble upward through the algae pond located above. In some embodiments, the combined duct and algae pond may be configured as an in-ground or an above-ground trench. Alternatively, the duct or ducts may be integrated underneath or laterally adjacent an algae pond that is wider than or otherwise shaped differently than the duct(s). In some embodiments, the duct(s) can be staged with gas booster pumps or compressors to assist the gas flow, which may be advantageous depending upon the length of the algae pond. The sparging of duct gas through the apertures may mix or agitate the algae pond, and thus enhance or promote algae growth.

In some traditional algae photobioreactor ponds, a paddle wheel or another apparatus is used to move the bulk of the pond water, e.g. algae slurry, at speeds that may be in the range of 0.2-0.4 meters/second (m/s) to mix and to maintain adequate mass transfer of gases and nutrients to/from the growing algae. Some embodiments of the disclosed systems may also include a paddle wheel or another suitable apparatus; however, as a result of the gas-driven mixing of the disclosed systems, it may be acceptable to reduce the load on the paddle wheel and resultant speed of the algae slurry (also called the pond speed) below the 0.2-0.4 m/s range and still maintain adequate mass transfer. Lower pond speeds can reduce the length of a pond required for a continuous process, which in some cases may be a 1-10 day residence time. Furthermore, gas sparging in the manner disclosed in the systems described herein may mix or agitate the algae slurry sufficiently so as to reduce the target flow speed for the algae slurry in the pond, thus using less pumping energy and potentially reducing the number of pumps and paddlewheels that might otherwise be required. Consequently, the flow speed to be maintained for the algae slurry may be 0.1 m/s or less for some embodiments and some operating conditions.

In some embodiments, the systems described herein may be configured to conduct flue gases through the gas duct(s). In addition to or in place of conducting flue gas, the duct(s) may be coupled to receive and distribute another gas that includes carbon dioxide ($CO_2$) or useable nitrogen when available. As examples, gas sources for the disclosed systems may include atmospheric air (whether concentrated or not) or an output from a Direct Air Capture (DAC) system.

Some traditional algae photobioreactor pond systems include traditional gas ducts, while others have no ducts. Depending on the chosen method of construction, the materials, fabrication, or installation costs for the disclosed ducting may be substantially less as compared to traditional gas ducting. In some examples, capital costs may be reduced by incorporating the construction of the unique duct arrangement into an algae pond construction process, as compared to installing a traditional duct, whether the traditional duct were to be installed later or even concurrently with the pond construction process. The terms "bioreactor" and "photobioreactor" may be used herein interchangeably.

Various algae bioreactors, e.g., ponds, configured as disclosed herein may be suited for operating continuously. Continuous operation may involve activities occurring through multiple growth cycles or growth periods of a selected variety or varieties of algae without clearing all algae from ponds 116 during the operation. Continuous operation may also include incremental harvesting of the algae as it matures or ripens. In some examples, one or more of the disclosed embodiments may be operated continuously for up to 90 days or longer and sometimes may be operated continuously for more or fewer days prior to stopping or pausing the system's operation for clean-out, for reconfiguration, or for another purpose. The suitability of the units for lengthy operations may provide an economic benefit. Even so, batch mode may also be used for at least some of the disclosed embodiments. A batch mode may include harvesting nearly all algae biomass and starting with a new supply of algae each week or every few weeks, according to a single growth cycle or growth period of the algae, as an example.

FIG. 1 is a schematic diagram of an example system 100 for growing algae, according to one or more embodiments. System 100 includes a photobioreactor 104, a gas collection device 106, and a duct system 108 that fluidically couples gas collection device 106 to photobioreactor 104. Photobioreactor 104 includes one or more ponds 116. In this example, photobioreactor 104 includes four ponds 116 which are configured as troughs or channels arranged parallel to each other. While four ponds 116 are depicted in system 100, more or less than four may be employed, without departing from the scope of the disclosure. Moreover, although ponds 116 are shown as straight, elongate troughs, which are rectangular when viewed from the top, one or more of ponds 116 may exhibit a different shape when viewed from the top, such as serpentine, rectangular, oval, ovoid, circular, semicircular, or any combination thereof.

Gas collection device 106 is configured to capture exhaust gas from a flue gas generating facility 114 and convey the flue gas to the photobioreactor 104. In some embodiments, the flue gas generating facility 114 may comprise a power plant, a furnace, an industrial process, a direct air capture system plant, or another source of carbon dioxide ($CO_2$). An apparatus 118 is also included for harvesting algae biomass from ponds 116.

Duct system 108 may include a duct inlet manifold 120 to distribute flue gas to each pond 116. In some embodiments, duct system 108 may further include a duct exit manifold (not shown) to collect unused flue gas from ponds 116, if any remains. The flue gas or other gas delivered through duct system 108 may be concentrated or not concentrated with respect to $CO_2$ and may be compressed or uncompressed, as compared to fluid conditions at the source of the gas or as compared to air at standard conditions. Gas compression may be used to reduce the volume transported, or to overcome pressure drop in system 100, or to balance flow between parallel paths leading multiple ponds 116, as examples. As used herein, the term "gas" refers to a single gas or a mixture of gases.

System 100 may further include a liquid handling system 110. As illustrated, liquid handling system 110 includes a pumping device 124, a reservoir 128, and fluid conveyance 130.

Liquid handling system 110 may be configured to operate on ponds 116 collectively or individually. In some embodiments, liquid handling system 110 may be fluidically coupled to photobioreactor 104 in at least two locations on each pond 116 to add and to withdraw portions of water or algae slurry to/from each pond 116. In at least one embodiment, liquid handling system 110 may be operated to induce flow, which may involve fluid recirculation, in one or more of ponds 116, which may improve mass transfer between the algae and its surroundings, or may be used to change a fluid level(s) in one or more of the ponds 116. Pumping device 124 may include a pump or a paddle wheel. Some embodiments include a paddle wheel in each pond 116, for example.

System 100 may further include a control system 112. Control system 112 may be configured with a controller, instrumentation, and machine-readable code to operate system 100. Control system 112 may be configured or otherwise programmed to control fluid flow in ponds 116 and to control liquid handling system 110, to maintain and adjust fluid level in ponds 116, and to monitor or control the pressure or flow rate of gases sparged into ponds 116, as examples. Though not shown, photobioreactor 104 may also include any of the following: suitable valving, a water supply, and other equipment to support algae growth and harvesting.

Figure 2:
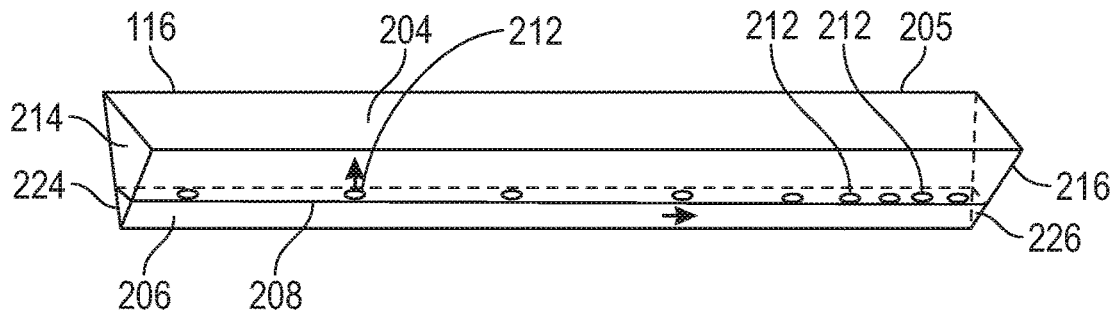
FIG. 2 illustrates an example photobioreactor for growing algae, according to various embodiments of the present disclosure.

FIG. 2 is an isometric side view of one of ponds 116 of FIG. 1, according to one or more embodiments. As illustrated, pond 116 may include a channel 204 that extends from a first end 214 to second end 216 and defines a pond volume to contain algae slurry. The top of channel 204 may be open to the atmosphere or, in various embodiments, may be closed or covered by a transparent cover, which may be vented to release oxygen that is produced. Pond 116 and channel 204 may be formed in a variety of cross-sectional shapes including square, trapezoidal, triangular, circular, semicircular, or any combination thereof, and would define an associated pond volume with a corresponding shape.

Pond 116 and channel 204 include a perimeter 205, which faces upward. Perimeter 205 includes a shape of an elongate rectangle, which may have a length to width (L:W) ratio of greater than or equal to 12:1. The pond volume of channel 204 is likewise characterized by the shape of an elongate rectangle with a length to width ratio that may be greater than or equal to 12:1. Various other embodiments of a photobioreactor that are in keeping with the present disclosure include a pond with a pond volume that include a perimeter having another shape, such as square, rectangular with L:W ratio less than 12:1, trapezoidal, triangular, circular, semicircular, oval (e.g., pill-shaped), ovoid, or any combination thereof. Thus, some embodiments include a pond with a pond volume shaped differently than the channel 204 depicted in FIG. 2. The choice of a cross-sectional shape or a perimeter shape for a pond, a channel, or a pond volume may be based on one or several considerations, such as factors associated with the available real estate (e.g., size, shape, topography, etc.), fluid flow considerations, the type of equipment or preferred arrangement of the equipment that may be installed to operate in conjunction with the pond, or factors associated with supplying materials to the pond, as examples.

Pond 116 may also include a duct 206 positioned adjacent the channel 204 to contain and circulate gas(es). In the illustrated embodiment, the duct 206 is positioned below the channel 204, but could alternatively be positioned on one or both lateral sides of the channel 204, without departing from the scope of the disclosure. Similar to channel 204, duct 206 may be formed in a variety of cross-sectional shapes including, but not limited to, square, trapezoidal, triangular, circular, semicircular, or any combination thereof. Moreover, while FIG. 2 shows a single duct 206 in conjunction with pond 116, more than one duct 206 may be employed beneath pond 116 or another pond, without departing from the scope of the disclosure.

Duct 206 extends from an inlet end 224 to a distal end 226. Inlet end 224 may be fluidically coupled to duct inlet manifold 120 (FIG. 1) receive flue gas. In embodiments where duct exit manifold is included in system 100 (FIG. 1), distal end 226 may be fluidically coupled to duct exit manifold to discharge excess flue gas. In other embodiments, distal end 226 may be sealed or otherwise capped to force all flue gas to exit duct 206 into channel 204.

A barrier 208 separates duct 206 from channel 204 and may form the bottom of channel 204 and/or the top of duct 206. Barrier 208 may be integral with a material or structure that defines the opposing ends 214, 216, the sidewalls and the bottom of the channel 204. In some embodiments, barrier 208 may be integral with a material or structure that defines the walls of duct 206. As examples, in some embodiments, barrier 208 may be integrated as a single unit with duct 206, like a collapsible hose or bladder. In some embodiments, the collapsible hose or bladder may be integrated as a single unit with channel 204. For some embodiments, barrier 208 may be formed of separate material from channel 204 and duct 206 and may be integrated with (e.g. attached to) channel 204 or duct 206 by an adhesive, by heat bonding, but stitching, or by any other suitable method.

Barrier 208 may include one or more apertures 212 that facilitate fluid communication between duct 206 and channel 204 to allow a portion of a gas in duct 206 to be selectively sparged into the pond volume. In contrast to prior membrane-type barriers that facilitate fluid (gas) flow through interstitial spacing within the material that provides a tortuous flow path subject to significant molecular forces, the apertures 212 described herein may comprise holes or orifices defined in the barrier 208. Apertures 212 may be stamped, formed, or defined in the barrier 208 by any suitable technique. As examples, in some embodiments, apertures 212 may be defined by the spacing between threads, strands, or wires in a fabric or a screen, which may be woven, bonded, or needled. One or more layers of fabric or screen may be used in any combination. In some embodiments, one or more of the apertures 212 may include or otherwise comprise a one-way check valve that facilitates fluid communication into channel 204 from duct 206, but prevents fluid communication from channel 204 into duct 206. While nine apertures 212 are depicted in FIG. 2, more or less than nine may be employed in pond 116, without departing from the scope of the disclosure.

In some embodiments, various parameters of apertures 212 may be optimized to maximize pressures and gas transfer between duct 206 and channel 204. Example parameters of apertures 212 that may be optimized include, but are not limited to, the spacing, quantity, size, or shape of apertures 212, or any combination thereof. Parameters of apertures 212 may be altered and otherwise optimized to adjust flow area for gas transfer, which may be selected to maintain a minimum target pressure in duct 206. In some embodiments, the parameters may vary along a length of barrier 208, corresponding to a length of duct 206, to compensate for flue gas pressure loss along the length of duct 206 and thereby may help achieve a uniform flow of gas into channel 204. Consequently, one or more parameters of apertures 212 may vary along a length of channel 204. For example, the distribution or spacing of apertures 212 may be graded or variable so that the spacing between adjacent apertures 212 near distal end 226 is less than the spacing between adjacent apertures 212 near inlet end 224. In such embodiments, the spacing between adjacent apertures 212 decreases from inlet end 224 to distal end 226 and may cause the flow area through barrier 208 to increase toward distal end 226.

Apertures 212 may have a uniform size or may have various sizes. Also, the flow area through apertures 212 at a given location along barrier 208 may be varied (e.g., increased) according to the intended depth of liquid in channel 204 for the given location. For embodiments that include a paddlewheel in channel 204, the flow area through apertures 212 located adjacent the inlet zone of the paddle wheel (where channel 204 may be relatively more shallow) may be less than the flow area through apertures 212 located adjacent the exit zone of the paddle wheel (where channel 204 may be relatively deeper). This difference in the aggregate flow area for the first apertures 212 as compared to the aggregate flow area of the second apertures 212 may result from a difference in the quantities of apertures, a difference in the sizes of the apertures, or a combination of these parameters.

Figure 3:
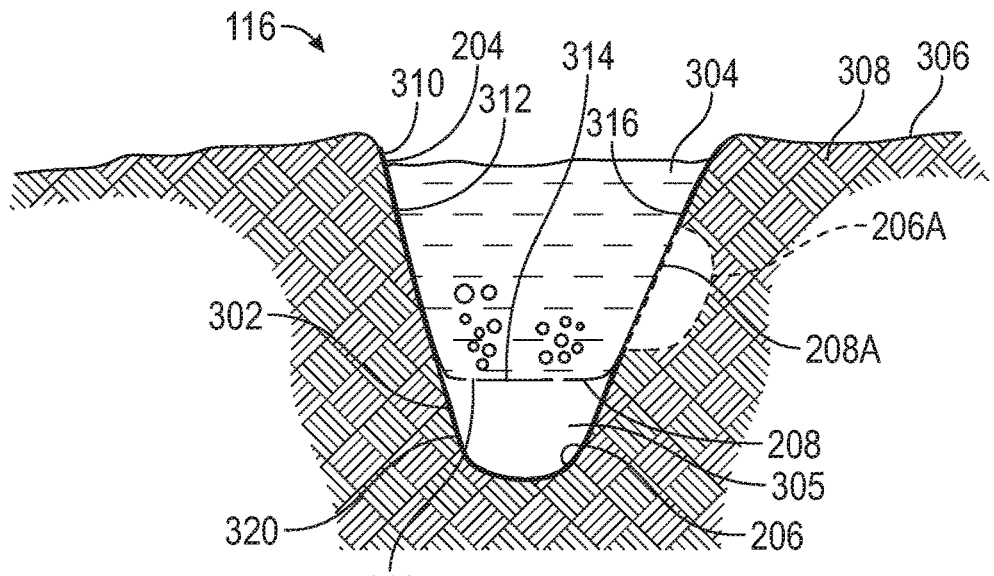
FIG. 3 is an end section view of the photobioreactor of FIG. 2 installed in an earthen trench, according to various embodiments of the present disclosure.

FIG. 3 is an end section view of pond 116 of FIG. 2, according to one or more embodiments. As illustrated, pond 116 may be defined or otherwise formed by an earthen trench 302. Trench 302 extends below the surface 306 of surrounding ground 308. In some embodiments, as illustrated, channel 204 may be wholly contained within trench 302 and otherwise entirely disposed below surface 306 of surrounding ground 308. In other embodiments, however, at least a portion of channel 204 may extend above surface 306. The walls of trench 302 may be formed by digging, piling, forming, or placing dirt, rock, or another suitable earthen, natural, or manmade material in a desired shape.

Pond 116 is shown containing an algae slurry 304 in channel 204 and duct 206 arranged adjacent (below) channel 204 within trench 302. In at least one embodiment, trench 302 may define duct 206. As illustrated, a flue gas 305 is circulating through duct 206 and is able to exit duct 206 through apertures 212. The gases discharged from apertures 212 act as sparging gases injected into channel 204.

In some embodiments, all or a portion of the walls of trench 302 may be lined with cement. In other embodiments, all or a portion of the walls of trench 302 may be lined with a sheet 310. In such embodiments, sheet 310 may help define or otherwise contain channel 204 of pond 116. As illustrated, sheet 310 extends along a first sidewall 312 of trench 302, a lower wall 314 that forms barrier 208, and a second opposing sidewall 316 of trench 302. Sheet 310 may be impermeable (except for apertures 212) to contain algae slurry 304 within channel 204.

In some embodiments, duct 206 may be formed and otherwise defined as part of trench 302. In such embodiments, the walls of duct 206 may comprise earthen walls. In other embodiments, however, duct 206 may be lined with a sheet 320 placed in the bottom of trench 302 and extending up the sides of trench 302 toward barrier 208. In at least one embodiment, sheet 320 may be bonded to sheet 310, but may sheets 310, 320 may alternatively be integrally fabricated to line the entire trench 302. The upper portions of sheet 320 may be compressed against trench 302 by sidewalls 312, 316, forming a seal to reduce or prevent gas leak. Sheet 320 may be mounted to trench 302 to keep it from moving or collapsing. Pond 116 and its trench 302 may have any of a variety of cross-sectional shapes including, as examples: square, trapezoidal, triangular, semicircular, or any combination thereof.

Sheets 310, 320 and barrier 208 may be impervious to water or gas, except at apertures 212. Sheets 310, 320 and barrier 208 may be made of a material that is flexible, rigid, or resilient. The material for the sheets 310, 320 and barrier 208 may include, but is not limited to, a polymer (e.g., high-density polyethylene or "HDPE", linear low-density polyethylene or "LLDPE"), a rubber or elastomer (e.g., ethylene propylene diene terpolymer or "EPDM"), a metal, a composite material (e.g., fiberglass), a woven material, or any combination thereof. In at least one embodiment, one or more of sheets 310, 320 and barrier 208 may comprise a plastic liner commonly used for algae ponds.

While duct 206 is shown generally arranged below channel 204, it is contemplated herein to arrange duct 206 on any adjacent surface of channel 204, without departing from the scope of the disclosure. In one or more embodiments, for example, a duct 206A (shown in dashed lines) may be located laterally adjacent pond 116 and channel 204 and a barrier 208A (shown in dashed lines) may interpose the duct 206A and the channel 204. More specifically, duct 206A and barrier 208A are shown between the sidewall of channel 204 and sidewall 316 of trench 302. Duct 206A and barrier 208A may be configured according to any of the options associated with duct 206 and barrier 208, respectively, and may be coupled or integrated with channel 204 as was previously described regarding duct 206 and barrier 208, respectively. For example, barrier 208A includes one or more apertures 212 (not shown) that are defined by and may be varied according to the parameters described elsewhere herein. In various embodiments, multiple ducts 206A and barriers 208A are locate laterally along various portions of the perimeter of a pond, whether the pond is shaped as a channel or differently than a channel.

Referring to FIGS. 1-3, operation of system 100 may be performed according to the concepts discussed above with respect to mixing in the algae slurry 304 and the resulting mass transfer, as may occur due to gas discharged from duct 206 into channel 204; and with respect to maintaining a travel speed for the algae slurry, as may be performed down the length of pond 116. The operational performance of pond 116 may be regulated using control system 112 according a predicted or perceived demand or growth rate in the algae. For example, flue gas pressure in duct 206 may be increased during hours of elevated or peak solar intensity to increase the flow rate of gas through the algae and provide increased mass transfer rates of $CO_2$ to the algae during time periods when the algae may grow faster. Control system 112 may control liquid handling system 110 to adjust a fluid level in one or more channels 204 (e.g., add or subtract algae slurry 304) in response to a pressure measured in duct 206. The trench 302 design may be used as a primary or as a solitary algae growth site in a facility such as system 100, or pond 116 may be used to conveying the flue gas to another algae growth site.

System 100 may be operated to maintain a balance between the gas pressure within duct 206 and the hydrostatic pressure of algae slurry 304 in channel 204, thus avoiding intrusion of water into duct 206 via apertures 212. The pressure in duct 206 may be high enough to allow gas from duct 206 to discharge into the algae slurry 304 via apertures 212, while simultaneously preventing the migration of liquids from the channel 204 into the duct 206. This may involve maintaining the gas pressure in duct 206 above a minimum target pressure, which may be greater than the hydrostatic pressure of the algae slurry 304 contained within channel 204.

Examples of operating conditions for some embodiments of system 100 include: 6 to 14 inches of depth for the water or algae slurry in channel 204 of pond 116 and a pressure in duct 206 maintained in the range of 0 (or slightly greater) to 30 inches of water column ("in. $H_2O$") greater than the hydrostatic pressure in channel 204. Combining the water depth and the additional pressure for duct 206, the net pressure in the duct 206 may range from 6 (or slightly greater) to 44 in. $H_2O$ in these examples. In at least some embodiments, the described pressure range for duct 206 may be implemented at distal end 226, while the pressure at inlet end 224 may be somewhat higher to overcome the pressure drop of gas flowing through the duct. Other depths of slurry in channel 204, greater or lesser, and other pressures, greater or lesser, for gas within duct 206 may be used in some examples.

Figure 4:
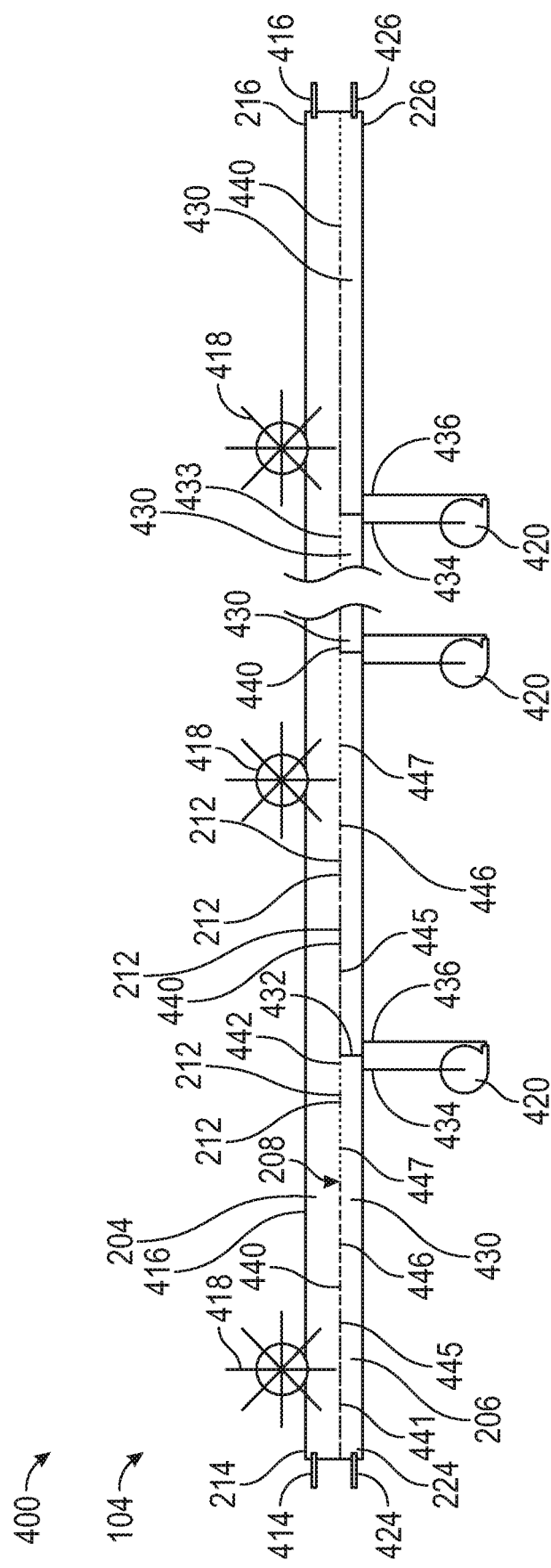
FIG. 4 is a side-view diagram of another example system for growing algae, according to various embodiments of the present disclosure.

FIG. 4 is a side-view diagram of another system 400 for growing algae, according to one or more additional embodiments. As illustrated, system 400 includes a photobioreactor 404, which may be similar in some respects to photobioreactor 104 of FIG. 1. In general, unless specifically described as being different, the configurations and the operations, including the potential variations, described for photobioreactor 104, are applicable to photobioreactor 404 of FIG. 4. Photobioreactor 404 may be installed in system 100 (FIG. 1) in place of or in addition to photobioreactor 104. Photobioreactor 404 includes a pond 416, one or more paddle wheels 418 installed in pond 416, and one or more blowers or gas booster pumps 420 fluidically coupled to pond 416 to aid the flow of gases through pond 416. Some embodiments of photobioreactor 404 may include a plurality of ponds 416 operating in parallel, for example, with each pond configured as described above.

Pond 416 is similar in some respects to pond 116 of FIGS. 1-3, and, more specifically, pond 416 may be an alternative embodiment of pond 116 according to various examples. Therefore, pond 416 may be best understood with reference to FIGS. 1-3, where like numerals will represent like components that may not be described again in detail. In general, unless specifically described as being different, the configurations and the operations, including the potential variations, described for pond 116, are applicable to pond 416. Similar to pond 116, for instance, pond 416 includes channel 204 to contain algae slurry, duct 206 to contain gas and positioned adjacent (e.g., below) the channel 204, and barrier 208 including one or more apertures 212 and separating duct 206 from channel 204.

Pond 416 is shown with additional features that were not described with respect to pond 116 (FIGS. 1-3), but may be incorporated in various embodiments of pond 116. For example, in pond 416 of FIG. 4, an inlet 414 for algae or water is included at first end 214, and an exit 416 for algae or water is included at second end 216. A gas inlet 424 is included at inlet end 224 of duct 206, and a gas exit 426 is included at distal end 226. More notably, in pond 416 gas duct 206 is divided into a plurality of duct zones 430, with each adjacent duct zone 430 being separated by a common bulkhead 432 configured to limit or prevent the flow of gas from one duct zone 430 to a neighboring duct zone 430. In at least some embodiments, bulkhead 432 is impermeable to the gas in duct 206.

Between each adjacent duct zone 430, a booster pump 420 is fluidically coupled from an intermediate gas exit 436 on one side of the corresponding bulkhead 432 to an intermediate gas inlet 434 on the opposite side of the same bulkhead 432. Booster pumps 420 may be operated to draw gas from a first duct zone 430 and discharge the gas in a subsequent duct zones 430 to overcome the pressure drop resulting from the flow of gas through the length of duct 206.

Barrier 208 may be installed in or may be integrated with channel 204 or with duct 206 as described above with respect to FIGS. 2 and 3. However, in this example barrier 208 is segmented. Similar to the division of duct 206, barrier 208 may be divided into a plurality of barrier segments 440. A corresponding barrier segment 440 is arranged in each duct zone 430, and each barrier segment 440 extends from a first end 441 proximal a gas inlet 424, 436 to a second end 442 proximal a gas exit 434, 426. The position of bulkheads 432 correspond to the transition from one barrier segment 440 to the next segment 440. The segmented barrier 208 may be a single piece that extends from duct inlet end 224 to distal end 226, or segments 440 may be made as separate pieces that seal end-to-end to form the full length of barrier 208 between ends 224, 226.

Each barrier segment 440 includes a plurality of apertures 212. The spacing, size, or shape of apertures 212 may vary along one or more of barrier segments 440 so that the flow area increases along a length of the barrier segment 440 from first end 441 to second end 442, which corresponds to a length of duct 206 and a length of channel 204. Some embodiments may include a steady increase in flow area along the length of a barrier segment 440 while some other embodiments include discrete changes in flow area. For example, the spacing between adjacent apertures 212 located near first end 441 of a given barrier segment 440 may be less than the spacing between adjacent apertures 212 located near second end 442. Alternatively, the size or shape of apertures 212 or a combination of these factors may vary. The variation in spacing, size, or shape distribution of apertures 212 along a given barrier segment 440 may compensate for pressure drop of gas as it flows through the corresponding duct zone 430 and thereby may help achieve a uniform flow of gas into the pond channel 204, along a length of that duct zone 430.

In some embodiments, a given barrier segment 440 may include a lengthwise first portion 445, a lengthwise second portion 446, and a lengthwise third portion 447, each portion 440, 445, 446 having a designed flow area through its corresponding apertures 212. Thus, each barrier segment 440 may be segmented. The second portion 446 includes a flow area that is greater than the flow area through first portion 445, and the flow area through third portion 447 is greater than the flow area through second portion 446.

EMBODIMENTS LISTING

The present disclosure provides, among others, the following embodiments, each of which may be considered as optionally including any alternate embodiments.

Clause 1. A system for growing algae that includes a photobioreactor that provides a channel configured to contain an algae slurry, a duct positioned adjacent the channel and configured to convey a gas, and a barrier separating the duct from the channel and providing one or more apertures to allow a portion of the gas to be injected into the algae slurry from the duct.

Clause 2. The system of clause 1, wherein the duct and at least a portion of the channel are formed in a trench of earthen material.

Clause 3. The system of clause 1, wherein the duct is positioned below the channel and the barrier is integrated with a bottom of the channel.

Clause 4. The system of clause 1, wherein the duct is positioned laterally adjacent the channel.

Clause 5. The system of any of the foregoing clauses, wherein the barrier is made of a material selected from a group consisting of a polymer, a rubber or elastomer, a metal, a composite material, a woven material, and any combination thereof.

Clause 6. The system of any of the foregoing clauses, wherein the one or more apertures comprise a plurality of apertures and one or more parameters of the plurality of apertures is varied along a length of the channel, and wherein the one or more parameters are selected from the group consisting of relative spacing, quantity, size, flow area, and shape of one or more of the plurality of apertures.

Clause 7. The system of any of the foregoing clauses, wherein the channel, the duct, and the barrier form a first pond of the photobioreactor and the photobioreactor further includes one or more additional ponds, each pond including a corresponding channel configured to contain the algae slurry, a corresponding duct positioned adjacent the corresponding channel and configured to convey the gas, and a corresponding barrier separating the corresponding duct from the corresponding channel and providing one or more apertures to allow a portion of the gas to be injected into the algae slurry from the corresponding duct, wherein a duct manifold is coupled to the corresponding duct of each pond to convey the gas into each duct.

Clause 8. The system of any of the foregoing clauses, further comprising a duct system that is fluidically coupled to receive the gas from a flue gas generating facility and to deliver the gas to the duct.

Clause 9. The system of any of the foregoing clauses, further comprising a liquid handling system configured to regulate a level of the algae slurry in the channel.

Clause 10. The system of any of the foregoing clauses, wherein the duct is separated into a plurality of duct segments along a length of the channel by one or more bulkheads, and wherein the barrier is divided into a plurality of barrier segments, one barrier segment being disposed above each duct segment, and a flow area through the one or more apertures varies along a length of at least one of the plurality of barrier segments.

Clause 11. The system of clause 10, further comprising a booster pump fluidically coupled between first and second duct segments of the plurality of duct segments to transport a portion of the gas past the bulkhead disposed therebetween.

Clause 12. A method, comprising: containing an algae slurry within a channel of a photobioreactor; conveying a gas within a duct positioned adjacent the channel, wherein the duct and the channel are separated by a barrier that provides one or more apertures; and injecting at least a portion of the gas into the algae slurry through the one or more apertures.

Clause 13. The method of clause 12, further comprising positioning the duct and at least a portion of the channel in a trench formed of earthen material.

Clause 14. The method of clause 12 or 13, wherein the one or more apertures comprise a plurality of apertures, the method further comprising varying one or more parameters of the plurality of apertures along a length of the channel.

Clause 15. The method of any of clauses 12 to 14, further comprising capturing the gas from a flue gas generating facility, and delivering the gas from flue gas generating facility to the duct via a duct system.

Clause 16. The method of any of clauses 12 to 15, further comprising adjusting a level of the algae slurry in the channel in response to a pressure in the duct.

Clause 17. A photobioreactor that includes a pond volume configured to contain an algae slurry, a duct positioned adjacent the pond volume and configured to convey a gas, and a barrier separating the duct from the pond volume and comprising a plurality of apertures through which the gas is injected into the algae slurry from the duct.

Clause 18. The photobioreactor of clause 17, wherein the pond volume is defined by a channel.

Clause 19. The photobioreactor of clause 17 or 18, wherein the duct is positioned laterally adjacent the channel the barrier is integrated with a sidewall of the channel.

Clause 20. The photobioreactor of any of clauses 17 to 19, wherein one or more parameters of the plurality of apertures is varied along a length of the duct, the one or more parameters being selected from the group consisting of relative spacing, quantity, size, flow area, and shape of one or more of the plurality of apertures.

Clause 21. The photobioreactor of any of clauses 17 to 20, wherein the duct is separated into a plurality of duct segments by one or more bulkheads, and wherein the barrier is divided into a plurality of barrier segments, one barrier segment being disposed above each duct segment, and one or more parameters of the plurality of apertures varies along a length of at least one of the plurality of barrier segments.

Clause 22. The photobioreactor of clause 21, further comprising a booster pump fluidically coupled between first and second duct segments of the plurality of duct segments to transport a portion of the gas past the bulkhead disposed therebetween.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms used herein, including the claims, have their plain, ordinary meaning unless otherwise explicitly and clearly defined by the patentee. Moreover, the indefinite articles "a" or "an," as used herein, including the claims, are defined herein to mean one or more than one of the element that it introduces.

The term "or" as used in a phrase such as "A or B" herein is intended to include optionally of any of the following: "A" alone, "B" alone, and, where feasible, "A and B." Ordinal numbers such as first, second, third, etc. do not indicate a quantity but are used for naming and reference purposes. In addition, ordinal numbers used in the claims in reference to a component or feature may differ from the ordinal numbers used in the written description for the corresponding component or feature. For example, a "second object" in a claim might be described as a "third object" or may be described without an ordinal number in the written description.

Unless otherwise indicated, all numbers expressing quantities of ingredients, properties such as length, volume, mass, molecular weight, operating conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

For the sake of clarity, not all features of a physical embodiment are described or shown in this application. It is understood that in the development of a physical embodiment incorporating the embodiments of the present disclosure, numerous implementation-specific decisions must be made to achieve the developer's goals, such as compliance with system-related, business-related, government-related, and other constraints, which vary by implementation and from time to time. While a developer's efforts might be time-consuming, such efforts would be, nevertheless, a routine undertaking for those of ordinary skill in the art and having benefit of this disclosure.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The illustrative embodiments disclosed herein suitably may be implemented in the absence of any element that is not specifically disclosed herein and/or any optional element disclosed herein. While components, compositions, and methods are described in terms of "comprising," "containing," or "including" various components or steps, the components, compositions, and methods can also "consist essentially of" or "consist of" the various components and steps. For the methods herein, the order of various process steps may be rearranged in some embodiments and yet remain within the scope of the disclosure, including the claims.

The invention claimed is:

1. A system for growing algae, comprising:
a photobioreactor that provides a channel configured to contain an algae slurry, the channel exhibiting a length greater than a width and having a first end and a second end opposite the first end;
a duct positioned adjacent the channel and extending between the first and second ends, the duct being configured to convey a gas; and
a barrier separating the duct from the channel and extending between the first and second ends, the barrier providing one or more apertures that allow the gas to be injected into the algae slurry from the duct,
wherein the duct provides a gas inlet at the first end for receiving the gas and a gas exit at the second end for discharging excess gas,
wherein the duct is separated into a plurality of duct zones along a length of the channel by one or more bulkheads, and
wherein the barrier is divided into a plurality of barrier segments, one barrier segment being disposed above each duct zone, and a flow area through the one or more apertures varies along a length of at least one of the plurality of barrier segments.

2. The system of claim 1, wherein the duct and at least a portion of the channel are formed in a trench of earthen material.

3. The system of claim 1, wherein the duct is positioned below the channel and the barrier is integrated with a bottom of the channel.

4. The system of claim 1, wherein the duct is positioned laterally adjacent the channel.

5. The system of claim 1, wherein the barrier is made of a material selected from a group consisting of a polymer, a rubber or elastomer, a metal, a composite material, a woven material, and any combination thereof.

6. The system of claim 1, wherein the one or more apertures comprise a plurality of apertures and one or more parameters of the plurality of apertures is varied along a length of the channel, and wherein the one or more parameters are selected from the group consisting of relative spacing, quantity, size, flow area, and shape of one or more of the plurality of apertures.

7. The system of claim 1, wherein the channel, the duct, and the barrier form a first pond of the photobioreactor and the photobioreactor further includes one or more additional ponds, each pond including:
a corresponding channel configured to contain the algae slurry;
a corresponding duct positioned adjacent the corresponding channel and configured to convey the gas; and
a corresponding barrier separating the corresponding duct from the corresponding channel and providing one or more apertures to allow a portion of the gas to be injected into the algae slurry from the corresponding duct, wherein a duct manifold is coupled to the corresponding duct of each pond to convey the gas into each duct.

8. The system of claim 1, further comprising a duct system that is fluidically coupled to receive the gas from a flue gas generating facility and to deliver the gas to the duct.

9. The system of claim 1, further comprising a liquid handling system configured to regulate a level of the algae slurry in the channel.

10. The system of claim 1, further comprising a booster pump fluidically coupled between first and second duct zones of the plurality of duct zones to transport a portion of the gas past the bulkhead disposed there between.

11. A method, comprising:
containing an algae slurry within a channel of a photobioreactor, the channel exhibiting a length greater than a width and having a first end and a second end opposite the first end;
receiving a gas at a gas inlet of a duct positioned adjacent the channel and extending between the first and second ends, wherein the duct and the channel are separated by a barrier also extending between the first and second ends and providing one or more apertures;
conveying the gas along the duct and injecting at least a portion of the gas into the algae slurry through the one or more apertures; and
discharging excess gas from the duct at a gas exit included at a distal end of the duct,
wherein the duct is separated into a plurality of duct zones along a length of the channel by one or more bulkheads, and
wherein the barrier is divided into a plurality of barrier segments, one barrier segment being disposed above each duct zone, and a flow area through the one or more apertures varies along a length of at least one of the plurality of barrier segments.

12. The method of claim 11, further comprising positioning the duct and at least a portion of the channel in a trench formed of earthen material.

13. The method of claim 11, wherein the one or more apertures comprise a plurality of apertures, the method further comprising varying one or more parameters of the plurality of apertures along a length of the channel.

14. The method of claim 11, further comprising:
capturing the gas from a flue gas generating facility; and
delivering the gas from flue gas generating facility to the duct via a duct system.

15. The method of claim 11, further comprising adjusting a level of the algae slurry in the channel in response to a pressure in the duct.

16. A photobioreactor, comprising:
a pond volume having a first end and a second end opposite the first end and configured to contain an algae slurry;
a duct positioned adjacent the pond volume and extending between the first and second ends, the duct being configured to convey a gas;
one or more bulkheads arranged within the duct and thereby dividing the duct into a plurality of duct zones;
a booster pump fluidically coupled between adjacent duct zones of the plurality of duct zones to draw a portion of the gas from one duct zone and inject the portion of the gas into another duct zone, wherein each bulkhead diverts the gas out of a corresponding one of the plurality of duct zones and toward a corresponding booster pump; and
a barrier separating the duct from the pond volume and extending between the first and second ends, the barrier comprising a plurality of apertures through which the gas is injected into the algae slurry from the duct.

17. The photobioreactor of claim 16, wherein the pond volume is defined by a channel.

18. The photobioreactor of claim 17, wherein the duct is positioned laterally adjacent the channel and the barrier is integrated with a sidewall of the channel.

19. The photobioreactor of claim 16, wherein one or more parameters of the plurality of apertures is varied along a length of the duct, the one or more parameters being selected from the group consisting of relative spacing, quantity, size, flow area, and shape of one or more of the plurality of apertures.

20. The photobioreactor of claim 16, wherein the barrier is divided into a plurality of barrier segments, one barrier segment being disposed above each duct zone, and one or more parameters of the plurality of apertures varies along a length of at least one of the plurality of barrier segments.

* * * * *